United States Patent [19]
Cartmell et al.

[11] Patent Number: 5,429,589
[45] Date of Patent: Jul. 4, 1995

[54] HYDROGEL GAUZE WOUND DRESSING

[75] Inventors: James V. Cartmell, Xenia; Wayne R. Sturtevant, Centerville; Michael L. Wolf, West Milton, all of Ohio

[73] Assignee: New Dimensions in Medicine, Inc., Dayton, Ohio

[21] Appl. No.: 862,456

[22] Filed: Apr. 2, 1992

[51] Int. Cl.⁶ .......................................... A61F 13/00
[52] U.S. Cl. ................................. 602/42; 602/48; 602/58; 602/75; 424/443; 523/111
[58] Field of Search .................. 602/42, 48, 58, 75; 604/307, 363; 424/443, 445, 446; 523/111

[56] References Cited

U.S. PATENT DOCUMENTS

| | | | |
|---|---|---|---|
| 2,772,999 | 12/1956 | Masci et al. | 424/445 |
| 2,858,830 | 11/1958 | Robins | 602/75 |
| 3,419,345 | 12/1968 | Parrish . | |
| 3,993,553 | 11/1976 | Assarsson et al. . | |
| 3,998,215 | 12/1976 | Anderson et al. . | |
| 4,246,139 | 1/1981 | Witt . | |
| 4,338,371 | 7/1982 | Dawn et al. . | |
| 4,389,211 | 6/1983 | Lenaghan . | |
| 4,569,861 | 2/1986 | Smith et al. . | |
| 4,685,909 | 8/1987 | Berg et al. . | |
| 4,717,378 | 1/1988 | Perrault et al. | 604/20 |
| 4,787,885 | 11/1988 | Binder . | |
| 4,838,885 | 6/1989 | Bernardin . | |
| 4,842,593 | 6/1989 | Jordan et al. . | |
| 4,842,597 | 6/1989 | Brook | 604/372 |
| 4,848,329 | 7/1989 | Dardik . | |
| 4,865,596 | 9/1989 | Weisman et al. . | |
| 4,909,244 | 3/1990 | Quarfoot et al. | 602/48 |
| 4,930,500 | 6/1990 | Morgan | 602/48 |
| 4,983,173 | 1/1991 | Patience et al. . | |
| 4,984,570 | 1/1991 | Langen et al. . | |
| 5,059,424 | 10/1991 | Cartmell et al. | 602/57 |
| 5,061,259 | 10/1991 | Goldman et al. . | |
| 5,087,242 | 2/1992 | Petelenz et al. | 128/802 |
| 5,112,618 | 5/1992 | Cartmell et al. | 424/443 |
| 5,115,801 | 5/1992 | Cartmell et al. | 602/48 |
| 5,135,472 | 8/1992 | Hermann et al. | 424/446 |

Primary Examiner—Paul Prebilic
Attorney, Agent, or Firm—Killworth, Gottman, Hagan & Schaeff

[57] ABSTRACT

The present invention provides a wound dressing in the form of a gauze or similar absorbent material having dehydrated hydrogel material impregnated therein for absorbing wound exudate. The dehydrated hydrogel material is formed from an aqueous mixture comprising: (a) from about 0% to about 90% by weight polyhydric alcohol; (b) from about 6% to about 60% by weight aliphatic diisocyanate terminated prepolymer; (c) from about 4% to about 40% by weight polyethylene oxide based polyamine; (d) 0% to about 2% by weight sodium chloride; and (e) the balance water. The present wound dressing is capable of absorbing large amounts of wound exudate without inhibiting the healing of the wound to which it is contacted since it does not adhere to such a wound.

2 Claims, 3 Drawing Sheets

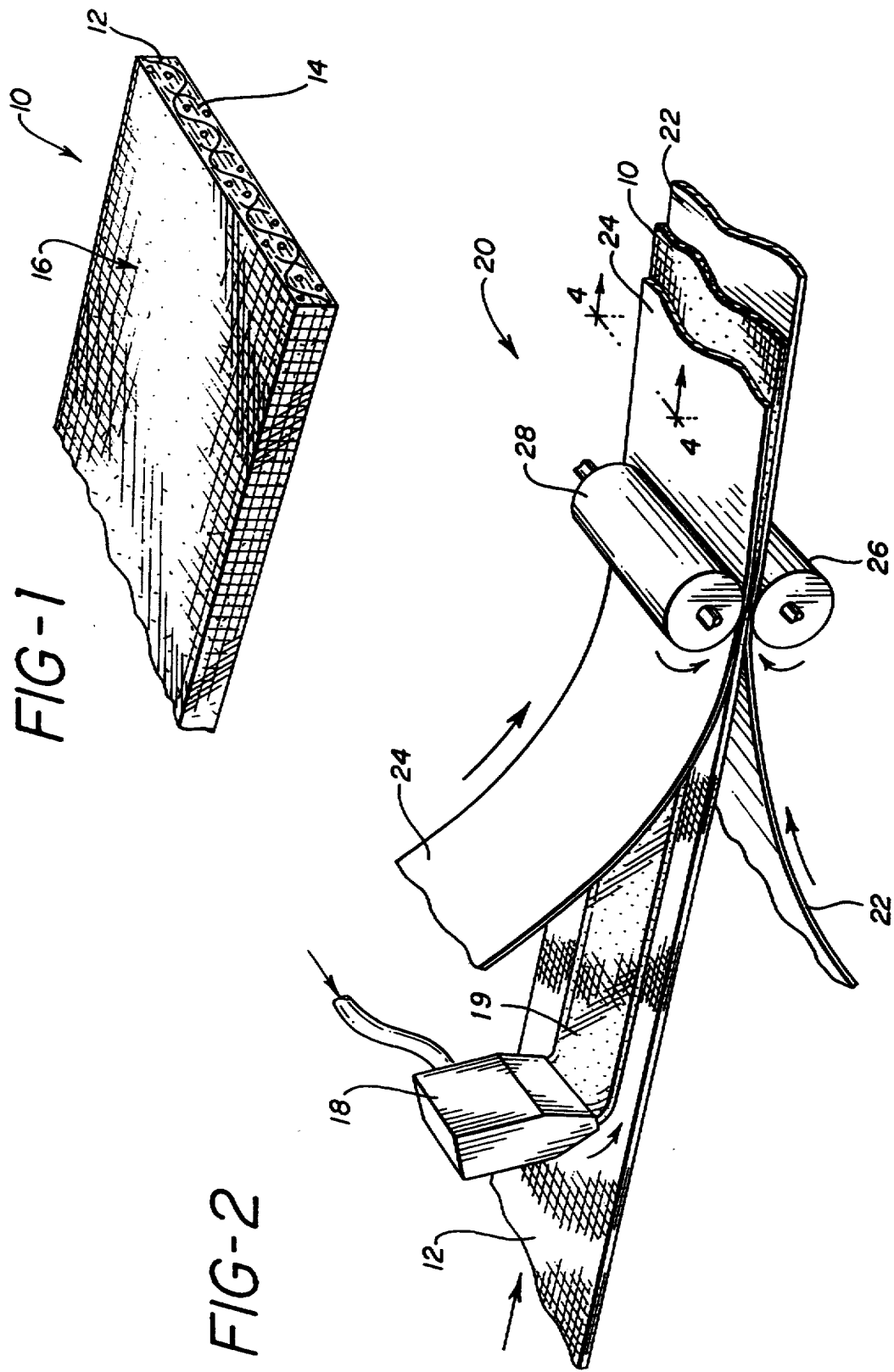

HYDROGEL GAUZE WOUND DRESSING

BACKGROUND OF THE INVENTION

The present invention generally relates to wound dressings and, more particularly, to a wound dressing in the form of gauze or similar absorbent material having a dehydrated hydrogel material impregnated therein for absorbing wound exudate.

Secreting skin wounds, such as decubitus ulcers and open surgical wounds, have long presented a medical challenge in keeping such wounds sterile and relatively dry. The accumulation of wound exudate, such as blood, pustulation, and other wound fluids, in wound crevices, promotes growth of bacteria and crusted organisms which cause infection and delay the healing process. Such wound exudate may also cause maceration of tissue adjacent the wound and support infection thereof. However, since it is often desirable to allow a wound to heal in a slightly "moist" or occlusive state, which is believed to accelerate healing, excess wound exudate must be removed. If excess wound exudate remains on a wound, a "blister" of exudate can form under the wound dressing which is not only unsightly, but also may cause the dressing to leak, thereby defeating the aim of sterility. However, existing methods of aspiration can lead to wound infection or can destroy sterility. Additionally, it is not desirable to remove all the exudate as that would result in a "dry" wound resulting in a slower healing process.

The art is replete with wound and/or surgical dressings for treating skin lesions, such as decubitus ulcers and open surgical wounds. For example, Mason, Jr. et al, U.S. Pat. No. 4,393,048, disclose a hydrogel wound treatment composition which dries to a powder after it is introduced into an open, draining wound to absorb wound exudate. However, dry hydrogel deteriorates as the wound fluids are absorbed resulting in lumping and uneven application. Additionally, such deteriorated lumps are difficult to remove from a wound site without damaging new cell tissue at the wound site. Furthermore, the progress of wound healing cannot be determined without removing, at least partially, the wound dressing from the wound site.

Aqueous moisture absorbing materials, such as a hydrogel material with a polyethylene glycol liquid curing agent as disclosed in Spence, U.S. Pat. No. 4,226,232, are easier to remove from the wound site, but cannot be sterilized by irradiation due to the formation of free radicals within the aqueous material. Another aqueous absorbing material used to absorb wound exudate is an hydrophilic polymer as disclosed in Rawlings et al, U.S. Pat. No. 4,657,006. Rawlings et al disclose a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound, thereby providing an excellent environment for bacteria proliferation.

In addition, wound dressings used in the past have not been conducive for healing extremely deep wounds and wounds having irregular shapes. To that end, wound dressings and surgical sponges formed from gauze and foam materials have been used for many years in surgical practice. These sponges and wound dressings have attempted to retain both the advantages of thin, soft and flexible single layer dressings and the absorptive cushioning and insulating properties of thicker pad-like structures. As a result, the sponges and wound dressings have traditionally been formed of multiple layers of thin, soft, low-count gauze material which are unified along fairly widely separated lines usually extending longitudinally or transversely.

Although such wound dressings and surgical sponges have been found useful in the past, none have provided the capability of absorbing large amounts of wound exudate without inhibiting the healing of the wound to which it is contacted. Most all of these dressings, including gauze and sponges, adhere to the wound upon removal, thereby damaging the wounds to which they are attached. This in turn prolongs the healing of such wounds. It would therefore be desirable to have a wound dressing having a structure which is thin, flexible and soft yet absorbs wound exudate in the same manner as the more thick pad-like wound dressings.

Accordingly, there is a need in the art for a wound dressing capable of absorbing large amounts of wound exudate without inhibiting the healing of the wound to which it is contacted. There is also a need for such a wound dressing which has a thin, flexible and soft structure so as to permit the wound dressing to be precut, sterilized, and readily available for application to a draining wound having irregular shapes and depths. Finally, there is a need for such a wound dressing which can be removed neatly as a single piece without adhering to the new cell tissue of the wound.

SUMMARY OF THE INVENTION

The present invention meets the aforementioned needs in the art by providing a wound dressing in the form of gauze or similar absorbent material having dehydrated hydrogel material impregnated therein for absorbing wound exudate. The present wound dressing is capable of absorbing large amounts of wound exudate without inhibiting the healing of the wound to which it is contacted by adhering to such a wound. The present wound dressing can be removed neatly as a single piece without experiencing any lumping or fragmentation of the dressing components.

In accordance with one aspect of the invention, a wound dressing having an absorbent layer impregnated with dehydrated hydrogel is provided. The wound dressing comprises a flexible absorbent layer capable of being secured to a wound on a patient. Further, the wound dressing includes a dehydrated hydrogel material impregnated in the absorbent layer such that the hydrogel material can absorb wound exudate upon contact with the wound. The term dehydrated as used herein is defined as a material substantially void of water. Further, the wound dressing may include an absorbent layer having interstices within which the dehydrated hydrogel material is impregnated. Preferably, the dehydrated hydrogel material is completely impregnated in the interstices such that the dehydrated hydrogel material is substantially exposed at the outer surface of the absorbent layer. In this way, the dehydrated hydrogel material is substantially in contact with the wound while contact of the absorbent layer thereto is minimized so as to preclude the absorbent layer from adhering to such a wound. This is desirable since healing of the wound is inhibited when the absorbent layer sticks or otherwise adheres to the new cell tissue forming in the wound. The absorbent layer may be formed from a material selected from the group consisting of fabrics, natural fibers, synthetic fibers, cellulose derivatives and combinations thereof.

In accordance with another aspect of the invention, a wound dressing comprising a flexible absorbent layer substantially in the form of a strip is provided. By forming the wound dressing in a strip, the absorbent layer is capable of being wrapped around a wound on a patient. The wound dressing also includes a dehydrated hydrogel material impregnated in the absorbent layer such that the dehydrated hydrogel material can absorb wound exudate upon contact with the wound. The wound dressing may include an absorbent layer having interstices within which the dehydrated hydrogel material is impregnated. In the preferred embodiment, the dehydrated hydrogel material is also completely impregnated in the interstices such that the dehydrated hydrogel material is substantially exposed at the outer surface of the absorbent layer. The absorbent layer in this embodiment may also be formed from a material selected from the group consisting of fabrics, natural fibers, synthetic fibers, cellulose derivatives and combinations thereof.

In accordance with yet another aspect of the present invention, a self-adhesive bandage is provided. The bandage comprises a substrate having first and second sides wherein the first side contacts a patient and includes a pressure sensitive adhesive coated onto at least one portion of the first side. The bandage further includes a wound dressing secured to the first side for contacting a wound on the patient. Preferably, the wound dressing component in the bandage also comprises a flexible absorbent layer capable of being secured to a wound on a patient, and a dehydrated hydrogel material impregnated in the absorbent layer such that the dehydrated hydrogel material can absorb wound exudate upon contact with the wound. Such a self-adhesive bandage provides a significant improvement over those used in the past since the wound dressing in the bandage does not stick or otherwise adhere to the wound so as to minimize destruction of the wound.

Accordingly, it is an object of the present invention to provide a wound dressing capable of absorbing large amounts of wound exudate without inhibiting the healing of the wound to which it is contacted; it is also an object of the invention to provide a wound dressing which possesses a thin, flexible and soft structure so as to permit the wound dressing to be precut, sterilized, and readily available for application to a draining wound having irregular shapes and depths; and, it is an object of the invention to provide a wound dressing which can be removed neatly as a single piece without adhering to the new cell tissue of the wound. Other objects and advantages of the invention will be apparent from the following detailed description, the accompanying drawings and the appended claims.

BRIEF DESCRIPTION OF THE DRAWINGS

FIG. 1 is a cross-sectional view of the wound dressing in accordance with the invention;

FIG. 2 is a schematic view illustrating a process by which the wound dressing of the invention can be made;

DETAILED DESCRIPTION OF THE PREFERRED EMBODIMENTS

Figure 3:
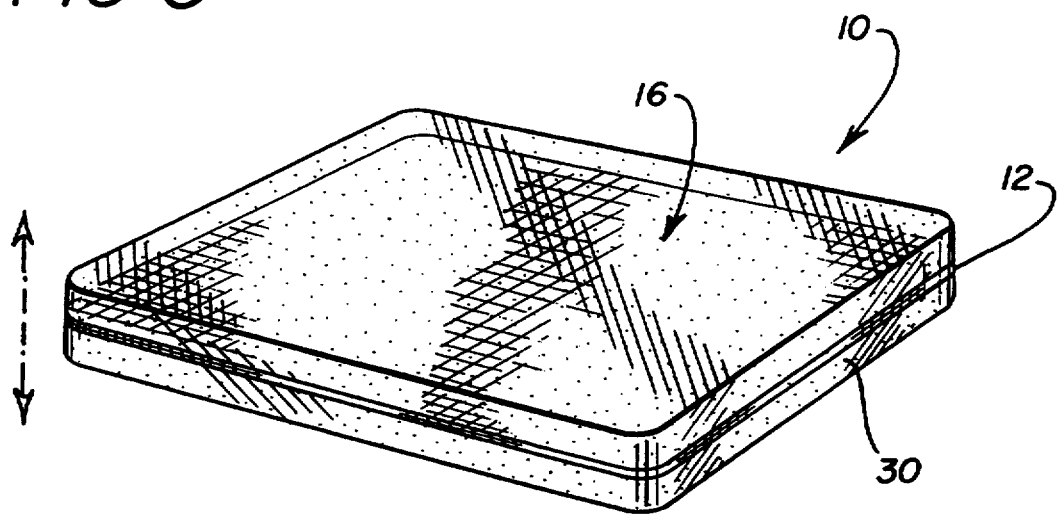
FIG. 3 illustrates the wound dressing after it has been applied to a draining wound.

The present invention provides a wound dressing 10 typically in the form of a thin, flexible gauze-like structure suitable for use in the treatment of wounds on a patient. As shown in FIG. 1, the wound dressing 10 comprises an absorbent layer 12 having dehydrated hydrogel material 14 impregnated therein for absorbing wound exudate. While those skilled in the art will appreciate the difficulty in illustrating the presence of the dehydrated hydrogel material 14 in the absorbent layer 12, it should be understood that the dehydrated hydrogel material 14 is preferably completely impregnated in the interstices of the absorbent layer 12. To that end, it is preferable for the absorbent layer 12 to be formed of any material capable of supporting the dehydrated hydrogel material 14. Those skilled in the art will appreciate that materials having interstices within which materials may be impregnated are particularly suitable for such purposes.

The dehydrated hydrogel material 14 must be able to adhere to the absorbent layer 12 so as to form a flexible, thin, gauze-like structure which, when contacted with a draining wound on a patient, absorbs large amounts of wound exudate without inhibiting the healing of such wound. The wound dressing 10 can be removed from the wound to which it is adhered in a non-destructive manner in that the wound dressing 10 does not adhere to the new cell tissue forming in the healing wound. The wound dressing 10 also does not break apart into fragments or lumps, but rather, can be removed substantially as a single piece. Such features have not been present in past thin, flexible, gauze-type wound dressings. These features are largely attributed to the hydrogel material from which the dehydrated hydrogel material 14 is formed. These materials are discussed more fully below.

While the wound dressing 10 is substantially in the form of a strip in FIG. 1, those skilled in the art should understand that other configurations are possible without departing from the scope of the invention. For example, wound dressing 10 may be formed such that, upon hydration of the dehydrated hydrogel material 14, the ultimate desired dimensions in terms of length, width and thickness of wound dressing 10 are achieved. Thus, those skilled in the art will appreciate that the initial dimensions of the wound dressing 10 can be tailored to the ultimate desired dimension of the wound dressing 10 in its hydrated form.

It is also preferable to have the dehydrated hydrogel material 14 completely impregnated in the interstices of the absorbent layer 12 such that the dehydrated hydrogel material 14 is substantially exposed at the outer surface 16 of the wound dressing 10 so that the absorbent layer 12 is precluded from adhering to the patient's wound. For purposes of minimizing the damage caused by such adherence of the absorbent layer 12 in the unlikely event that it contacts the wound in which the wound dressing 10 is disposed, the absorbent layer 12 is preferably formed from a material selected from the group consisting of fabrics, natural fibers, synthetic fibers, cellulose derivatives and combinations thereof. The preferred materials should also provide a sufficient support matrix for impregnation of the dehydrated hydrogel material 14.

For purposes of providing a more intuitive understanding of the wound dressing 10, a process 20, by which the wound dressing 10 can be made, is schematically illustrated in FIG. 2. As seen in FIG. 2, the absorbent layer 12 is fed in sheet form under an applicator 18 capable of receiving and applying a liquid or uncured hydrogel material 19 without permitting it to cure within its components. The applicator applies the uncured hydrogel material 19 onto the absorbent layer 12 in an amount just sufficient to impregnate the interstices therein. As those skilled in the art will appreciate, the amount of uncured hydrogel material 19 applied will vary with the particular material used as the absorbent layer 12 and the size of the sheet to be coated. It is preferable for a pair of release sheets 22 and 24 to encompass the absorbent layer 12 so as to provide protection for subsequent processing.

A pair of rollers 26 and 28 cooperate with one another to compress the release sheets 22 and 24 together such that the uncured hydrogel material 19 spreads evenly on and into the absorbent layer 12. Preferably, the release sheets 22 and 24 are releasably secured to the absorbent layer 12 such that they may be removed prior to use or packaging. FIG. 2 illustrates the wound dressing 10 having the absorbent layer 12 impregnated with the uncured hydrogel material 19 which is sandwiched between the release sheets 22 and 24. The uncured hydrogel material 19 is then allowed to cure to form a hydrated hydrogel material 30 (FIG. 3). Thereafter, the wound dressing 10 is dried, oven-baked or otherwise dehydrated so as to evaporate the water contained in the hydrogel material 30. Obviously, the release sheets 22 and 24 will be removed prior to whichever dehydrating process is used. The result is a finished wound dressing 10 containing the dehydrated hydrogel material 14 capable of fulfilling the purposes and objects outlined herein.

Figure 4:
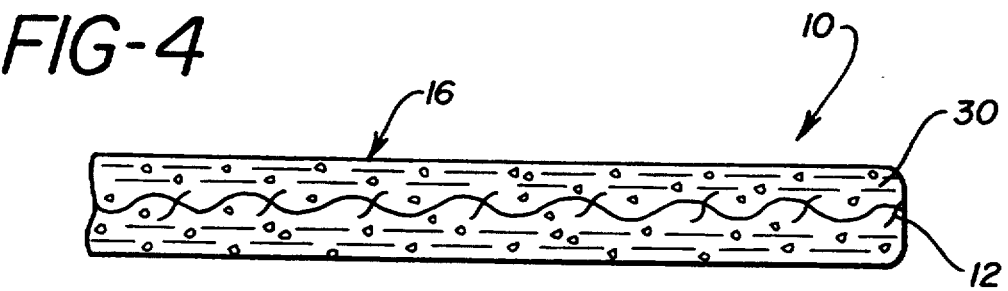
FIG. 4 is a cross-sectional view of the wound dressing depicted in FIG. 3.

Referring now collectively to FIGS. 3 and 4, the wound dressing 10, after having been contacted with a draining wound, is illustrated. FIG. 3 attempts to illustrate the expansion or swelling of the dehydrated hydrogel material 14 upon acquisition of bodily fluids, such as wound exudate, from the wound to which the wound dressing 10 is secured. The expanded or hydrated hydrogel material is referred to herein by reference numeral 30. The wound dressing 10 is therefore analogous to a sponge in that its initial dehydrated version depicted in FIG. 1 expands as fluids are absorbed to form the wound dressing 10 containing the hydrogel material 30. FIG. 4 is a cross-sectional view of the wound dressing 10 depicted in FIG. 3 and shows the hydrogel material 30 swelled in and around the absorbent layer 12.

As those skilled in the art will appreciate, the hydrogel material 30 depicted in FIG. 3 is the same as the cured hydrogel material 30 discussed with respect to the process 20 by which the wound dressing 10 is made. In essence, the hydrogel material 30 in process 20 is dehydrated after which it is returned to its original hydrated state upon wound exudate absorption and again referred to herein as the hydrogel material 30. In any event, the preferred hydrogel material 30 is formed from an aqueous mixture of polyhydric alcohol, an aliphatic diisocyanate terminated prepolymer, polyethylene oxide based diamine and sodium chloride. Preferably, the polyhydric alcohol is selected from the group consisting of polypropylene glycol, polyethylene glycol and glycerine. The hydrogel material 30 in its dehydrated state, which is referred to herein as the dehydrated hydrogel material 14, provides a highly absorbent material capable of retaining large amounts of wound exudate, thereby rendering it very suitable for use in wound dressings. By forming the hydrogel material 30 from the aforementioned aqueous mixture, the wound dressing 10 remains intact as it absorbs wound exudate from the wound.

Moreover, the hydrogel material 30 does not adhere or stick to the wound thereby allowing for easy removal of the wound dressing 10 substantially as a single piece. Additionally, the biocompatibility of the hydrogel material 30 within the wound is extremely favorable. Thus, the resulting hydrogel material 30, and therefore the dehydrated hydrogel material 14, provides a bio-compatible, non-irritating, fluid absorbing, bacterial protective, cushioning, skin-like media over the wound site. An additional advantage of the hydrogel material 30 is that it may be transparent, rendering it possible to inspect the wound site through the absorbent layer 12 without removing the wound dressing 10.

The preferred aliphatic diisocyanate terminated prepolymer is an isophoronediisocyanate terminated prepolymer based on polyols containing more than about 40% polyethylene oxide and having an isocyanate content of about 3% by weight. The molecular weight of the isophoronediisocyanate terminated prepolymer is preferably in a range from about 1500 to about 8000 and most preferably, from about 4000 to about 5000. The polyethylene oxide based polyamine is preferably a polyethylene oxide based diamine having a molecular weight in a range from about 200 to about 6000 and most preferably, about 2000. It is also preferable that the aliphatic diisocyanate terminated prepolymer and the polyethylene oxide based polyamine have a stoichiometric ratio of about 1:1. Those skilled in the art will appreciate that all of the constituents with the preferred hydrogel material may be readily synthesized or purchased commercially neither of which is more preferred.

It has been found that a more preferred hydrogel material 30, and therefore the dehydrated hydrogel material 14, is formed from an aqueous mixture including from about 0% to about 90% by weight polyhydric alcohol; from about 6% to about 60% by weight aliphatic diisocyanate terminated prepolymer; from about 4% to about 40% by weight polyethylene oxide based polyamine; up to about 2% by weight sodium chloride; and the balance water. A more preferred hydrogel composition for forming the hydrogel material 30 is formed from a mixture comprising from about 15% to about 30% by weight polypropylene glycol; from about 8% to about 14% by weight isophoronediisocyanate terminated prepolymer; from about 5% to about 10% by weight polyethylene oxide based diamine; and up to about 1% by weight sodium chloride; and the balance water. Most preferably, the hydrogel material 30 is formed from a mixture comprising: (a) from about 16% to 17% by weight polypropylene glycol; (b) from about 10% to 12% by weight isophoronediisocyanate terminated prepolymer; (c) from about 7% to 9% by weight polyethylene oxide based diamine; (d) about 0.5% to 1% by weight sodium chloride; and (e) the balance water.

The aforementioned preferred hydrogel compositions provide a wound dressing 10 having the desired properties of excellent biocompatibility and absorption of exudate properties without adhering to the wound. However, other materials having such characteristics, including but not limited to the aforementioned hydrogel compositions, may be used to form the hydrogel material 30 in accordance with the present invention.

Figure 5:
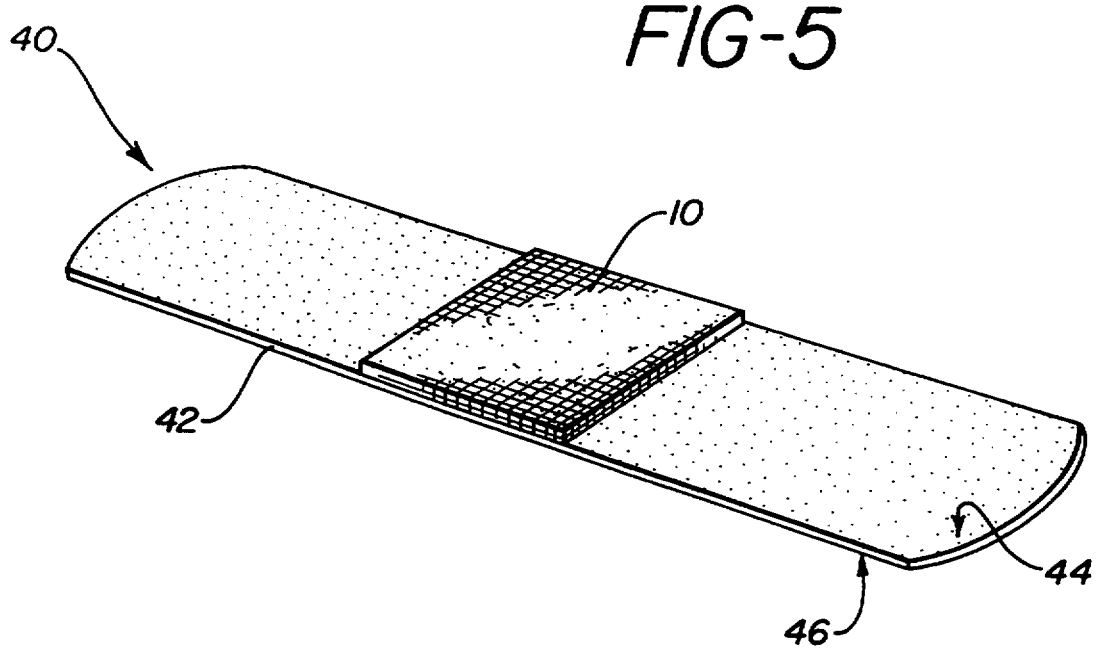
FIG. 5 is a perspective view of a conventional self-adhesive bandage incorporating the wound dressing of the invention.
Figure 6:
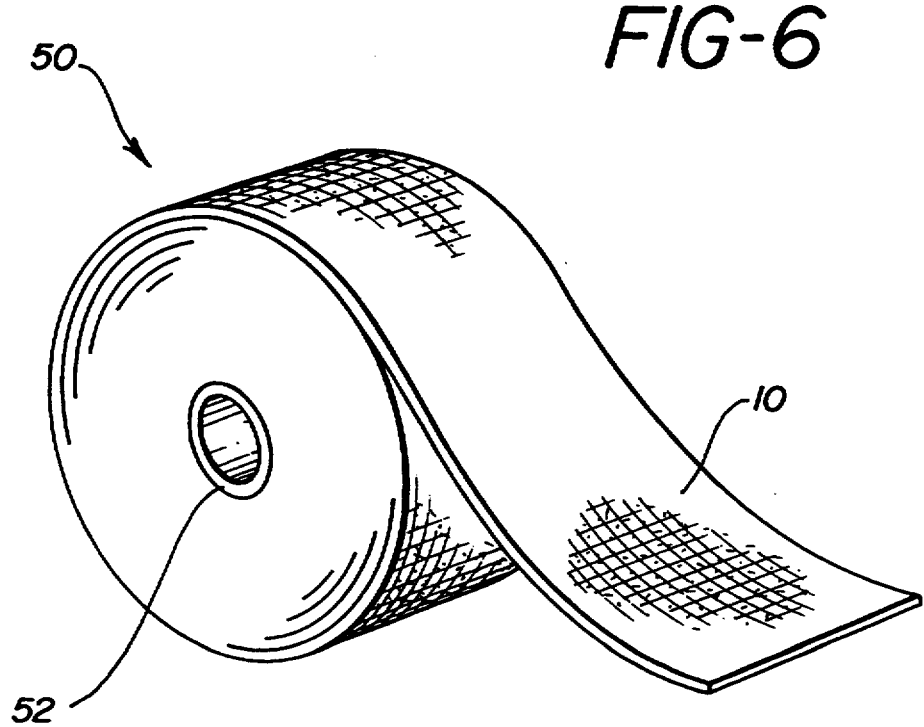
FIG. 6 is a perspective view of the wound dressing in the form of a roll dispenser which can be easily and quickly accessed when treating wounds.

While the wound dressing 10 of the present invention may serve as an extremely viable wound dressing by itself, the wound dressing 10 may also be incorporated into other wound dressings in order to improve their performance. By way of example only, a few of such wound dressing embodiments are illustrated in FIGS. 5 and 6. FIG. 5 illustrates the use of the wound dressing 10 in a bandage 40 of the self-adhesive type. The self-adhesive bandage 40 comprises a substrate 42 having first and second sides 44 and 46, respectively, wherein the side 44 contacts a patient and includes a pressure sensitive adhesive coated onto at least one portion of side 44.

As seen in FIG. 5, the bandage 40 has pressure sensitive adhesive coated over all portions which ultimately contact the patient. The bandage 40 also includes the wound dressing 10 secured to the side 44 for contacting a wound on the patient. Preferably, the wound dressing 10 performs and is formed as described above with respect to FIGS. 1-4. In this way, the wound dressing 10 in the bandage 40 swells as it absorbs wound exudate from the wound to which it is attached. It should be understood that the bandage 40 may include additional materials other than that of which is described herein without departing from the scope of the invention.

Turning now to FIG. 6, the wound dressing 10 is illustrated in the form of a roll dispenser 50. The wound dressing 10 is formed as described above with respect to FIGS. 1-4 and then wrapped about a spool 52 or similar device such that the wound dressing 10 can be easily accessed. As a result, the roll dispenser 50 facilitates quick and easy access to the wound dressing 10 in that a user can cut a sufficient amount of the wound dressing 10 to treat a wound on a patient. It should now be apparent to those skilled in the art that the wound dressing 10 can be used in a wide variety of existing wound dressings as well as on its own.

Having described the invention in detail and by reference to preferred embodiments thereof, it will be apparent that modifications and variations are possible without departing from the scope of the invention which is defined in the appended claims. For example, the wound dressing 10 can be employed in other wound dressings beyond those of which are described herein.

What is claimed is:

1. A wound dressing comprising:
   a flexible absorbent layer capable of being secured to a wound on a patient, said flexible absorbent layer comprising a gauze material; and
   a dehydrated hydrogel material which is void of water, said hydrogel material being impregnated in said absorbent layer such that said hydrogel material can absorb wound exudate upon contact with said wound.

2. A wound dressing comprising:
   a flexible absorbent layer substantially in the form of a strip such that said absorbent layer is capable of being wrapped around a wound on a patient, said flexible absorbent layer comprising a gauze material; and
   a dehydrated hydrogel material which is void of water, said hydrogel material being impregnated in said absorbent layer such that said hydrogel material can absorb wound exudate upon contact with said wound.

* * * * *